US00PP16153P3

(12) United States Plant Patent
Perkins

(10) Patent No.: US PP16,153 P3
(45) Date of Patent: Dec. 13, 2005

(54) ***ANGELONIA* PLANT NAMED 'CART WHITE'**

(50) Latin Name: *Angelonia angustifolia*
Varietal Denomination: Cart White

(75) Inventor: Ralph Tyler Perkins, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 501 days.

(21) Appl. No.: 10/400,116

(22) Filed: Mar. 25, 2003

(65) Prior Publication Data

US 2004/0194180 P1 Sep. 30, 2004

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Michelle Kizilkaya
(74) *Attorney, Agent, or Firm*—Jondle & Associates P.C.

(57) ABSTRACT

An *Angelonia* cultivar particularly distinguished by white colored flowers, compact habit and good basal branching.

1 Drawing Sheet

Genus and species: *Angelonia angustifolia.*
Variety denomination: 'Cart White'.

BACKGROUND OF THE NEW PLANT

The present invention comprises a new and distinct cultivar of *Angelonia,* botanically known as *Angelonia angustifolia*, and hereinafter referred to by the cultivar name 'Cart White'. The new culivar is asexualy reproduced from vegetative cuttings and tissue culture resulting from the cross of the seed/pod parent 'AngelMist Purple Stripe', a purple and white bicolor commercial line that is unpatented ×'AngelMist Lavender', a lavender commercial line that is unpatented.

'Cart White' is a product of a planned breeding program intended to create new *Angelonia* plants with white colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half-year period. The plant has also been trialed at Gilroy, Calif., Litchfield, Mich. and Andijk, The Netherlands. The present invention has been found to retain its distinctive characteristics through successive propagations; and this novelty is firmly fixed.

DESCRIPTION OF PHOTOGRAPH

This new *Angelonia* plant is illustrated by the accompanying photograph which shows blooms, buds, and foliage of the plant in full color, the colors shown being as true as can be reasonably obtained by conventional photographic procedures.

The Photograph shows the mature inflorescence.

DESCRIPTION OF THE NEW CULTIVAR

The following detailed descriptions set forth the distinctive characteristics of 'Cart White'. The data, which defines these characteristics, were collected from asexual reproductions carried out in Gilroy, Calif. The plant history and photograph was taken on 10 months old plants grown in one-gallon pots in fall/winter season, in a poly-covered greenhouse under 2–4 supplemental light and color readings were taken in the greenhouse in the winter season under natural light. Plants had been cut back numerous times prior to data readings taken. All major branches are cut back about 10–20 cm to keep the plant from becoming unruly. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.—Angelonia angustifolia.*
*Commercial.—Angelonia.*
Form: Upright and erect.
Growth and branching habit: Good vigorous habit, well branched, pinching 1–2 times after transplant enhanced branching.
Height: From soil level to top of blooms: Approximately 50–60 cm.
Width: Approximately 30–45 cm including flowers.
Time to produce a finished flowering plant: 8–10 weeks for a 4–6 inchpot.
Outdoor plant performance: Full sun, free-flowering through the summer, some heat tolerance. Use in mixed container plantings, or mass planting in a bed.
Time to initiate roots: Approximately 18–23 days at warm temperatures.
Root description: Fibrous, free branching.

THE LEAVES

Arrangement: Opposite.
Length: 4.5–4.8 cm.
Width: 0.8–1.0 cm.
Leaf blade shape: Linear.
Leaf margin: Serrate.
Apex shape: Acute.
Base shape: Cuncate.

Mature leaf color: Upper side, between RHS 137A and B (green); Underside, RHS 137C (green) with RHS 145C (yellow-green) mid-vein.
Juvenile leaf color: Upperside between RHS 143B and C; Underside, RHS 143C.
Texture: Many glandular hairs of various sizes, many with a dark yellow hue, physically leaving a sticky residue.
Venation: Pinnate.
Venation color: RHS 145B (yellow-green).

THE STEM

Length: 50–60 cm from base of plant to tip of branch.
Diameter: 0.25–0.5 cm taken from the lower ⅓ of the stem.
Internodes length: 0.7–2.0 cm.
Branch aspect: 45–60 degree.
Color: RHS 144B (yellow-green).
Texture: Many glandular hair of various sizes, many with a dark yellow hue.
Stem anthocyanin: No.
Pedicel color: RHS 144C (yellow-green).
Pedicel length: 1.1–1.5 cm.
Pedicel diameter: 0.1 cm.
Pedicel texture: Many glandular hairs of various sizes, many with a dark yellow hue.
Aspect: 45–60 degrees.

THE BUD

Shape: Orbicular.
Diameter: 0.4–0.6 cm.
Length: 0.5–0.6 cm.
Color at tight bud: RHS 2C (yellow).

THE FLOWER

Blooming habit: Continuous throughout the growing season. Good floriferousness.
Floret and inflorescence type: Single, 2 lipped (5-petaled, fused at base) flowers, solitary in a leaf axis, on a terminal raceme.
Flower color, upper side: Pure white.
Flower color, underside: Pure white.
Corolla color inside: Pure white with a spot of RHS 143A (green) at the back of the lower portion of the corolla.
Florets per raceme: 16–40.
Floret diameter: 2.1–2.5 cm.
Petal size, upper lip, 1 petal, and length: 0.6–0.7 cm from the corolla opening; width 0.6–0.7 cm.
Lower lip, lateral petal, and length: 0.9 cm from the corolla opening; width 0.9 cm.
Lower lip, mid-petal, length: 1.9–2.1 cm from ovary; width 0.7–0.8 cm.
Petal base: Fused.
Petal margin: Entire.
Petal texture: Papillose and short glandular hairs, many with a yellow-green hue.
Sepals: 5, fused at base.
Sepal color: RHS 143A (green).
Sepal length: 0.3–0.5 cm.
Sepal width: 0.1 cm.
Sepal shape: Ovate.
Sepal apex: Ocute.
Sepal anthocyanin: No.
Sepal texture: Many short glandular hairs, many with a yellow-green.
Lastingness of individual blooms: 6–9 days.
Fragrance: None.

THE REPRODUCTIVE ORGANS

Stamens: 4, in pairs.
Filament color: Pure white.
Pollen color: RHS 161A (greyed-yellow).
Pollen amount: Moderate.
Pistil: One.
Stigma: Pure white.
Style color: Pure white.
Fruit seed set: Not observed.

DISEASE AND INSECT RESISTANCE

Not observed.

COMPARISON WITH KNOWN CULTIVARS

'Cart White' differs from the female parent, 'AngelMist Purple Stripe', in the following ways: 'Cart White' has a fuller and freer branching habit, is freer flowering and has a white colored flower and 'AngelMist Purple Stripe' has a white with purple striped flower.

'CartWhite' differs from the male parent, 'AngelMist Lavender' in the following ways: 'Cart White' has a larger flower, is more upright and has a fuller and freer branching habit than 'AngelMist Lavender'.

I claim:

1. A new and distinct *Angelonia* plant as shown and described herein.

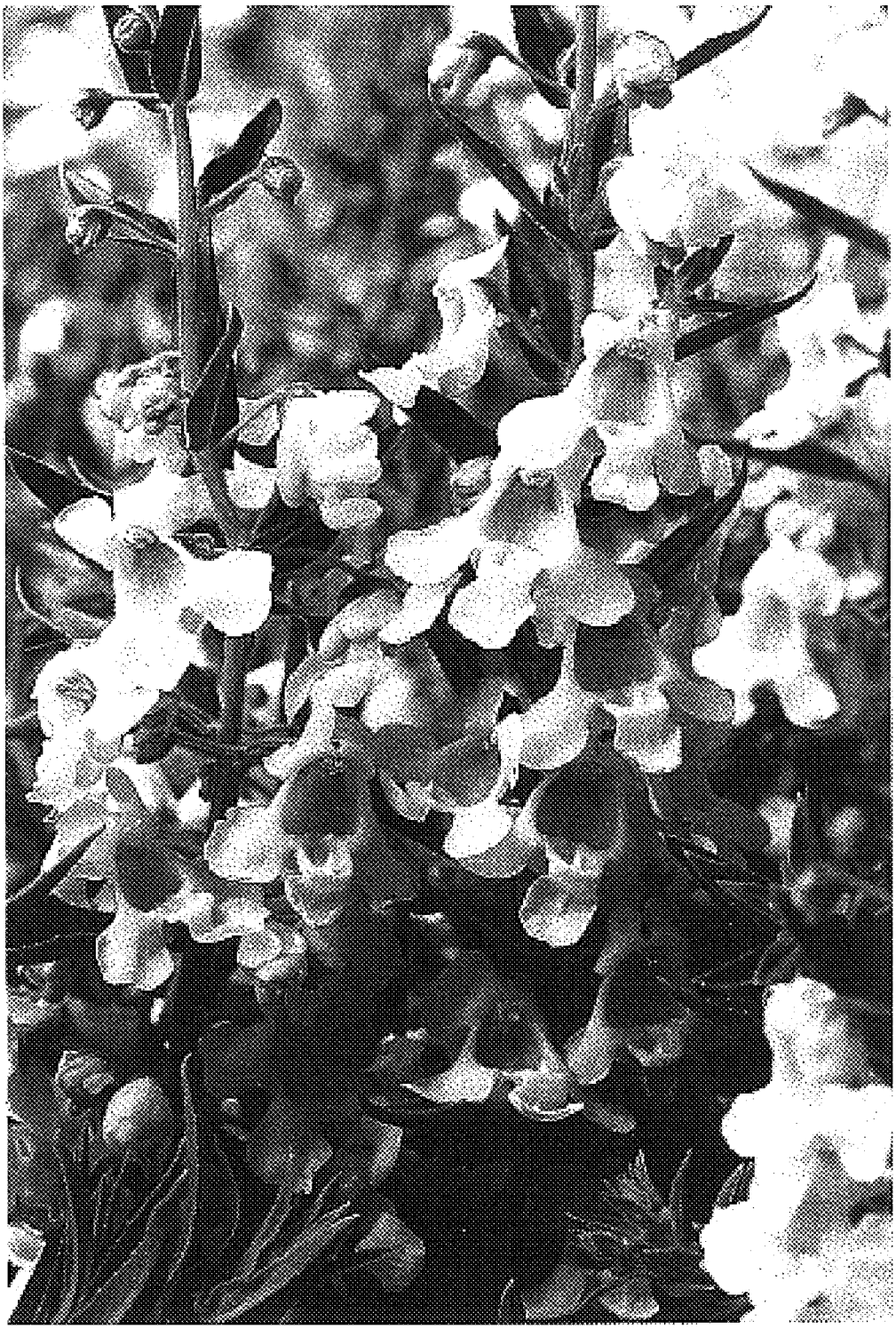

* * * * *